United States Patent
Yao et al.

(10) Patent No.: US 9,101,943 B2
(45) Date of Patent: Aug. 11, 2015

(54) CENTRIFUGAL PARTICLE SEPARATION AND DETECTION DEVICE

(71) Applicant: National Tsing Hua University, Hsinchu (TW)

(72) Inventors: Da-Jeng Yao, Hsinchu (TW); Chih-Chung Chen, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 52 days.

(21) Appl. No.: 13/706,021

(22) Filed: Dec. 5, 2012

(65) Prior Publication Data

US 2014/0045249 A1 Feb. 13, 2014

(30) Foreign Application Priority Data

Aug. 9, 2012 (TW) .............................. 101128806 A (51) Int. Cl.
| | |
|---|---|
| B04B 7/08 | (2006.01) |
| G01N 15/02 | (2006.01) |
| B01L 3/00 | (2006.01) |
| C12M 3/00 | (2006.01) |
| G01N 35/00 | (2006.01) |
| G01N 15/04 | (2006.01) |
| C12M 1/26 | (2006.01) |
| G01N 15/00 | (2006.01) |

(52) U.S. Cl.
CPC .............. *B04B 7/08* (2013.01); *B01L 3/502753* (2013.01); *G01N 15/0272* (2013.01); *B01L 2300/0681* (2013.01); *B01L 2300/0803* (2013.01); *B01L 2300/0864* (2013.01); *B01L 2400/0409* (2013.01); *B01L 2400/086* (2013.01); *C12M 1/264* (2013.01); *G01N 15/042* (2013.01); *G01N 35/00069* (2013.01); *G01N 2015/0053* (2013.01); *G01N 2015/0288* (2013.01)

(58) Field of Classification Search
USPC .......................... 422/415, 506, 72, 533, 548
See application file for complete search history.

(56) References Cited

U.S. PATENT DOCUMENTS

| | | | | |
|---|---|---|---|---|
| 5,173,262 | A * | 12/1992 | Burtis et al. | 422/72 |
| 7,141,416 | B2 * | 11/2006 | Krutzik | 435/288.5 |
| 2003/0059341 | A1 * | 3/2003 | Gazeau | 422/64 |
| 2007/0190520 | A1 * | 8/2007 | Wolf et al. | 435/4 |
| 2007/0224591 | A1 * | 9/2007 | Gui et al. | 435/4 |
| 2008/0056949 | A1 * | 3/2008 | Lee et al. | 422/72 |
| 2009/0081773 | A1 * | 3/2009 | Kaufman | 435/309.1 |

OTHER PUBLICATIONS

Chih-Chung Chen et al., "Particle Size Based Separator via Concentric PDMS Structure", Symposium on Engineering Medicine and Biology Applications & International Workshop on Bio-inspired System and Prosthetic Devices, Feb. 10-13, 2012, Taichung, TW.

* cited by examiner

*Primary Examiner* — Jennifer Wecker
(74) *Attorney, Agent, or Firm* — WPAT, P.C.; Anthony King; Kay Yang (57) ABSTRACT

The present invention provides a centrifugal particle separation and detection device, which can separate and detect particles according to the particle size. The centrifugal particle separate and detection device is practiced with a centrifuge to separate particles, and can be applied to cancer cell detection, blood lymphocyte isolation, tissue engineering, polynucleotide hybridization, microorganism separation and detection and fine chemical purification.

9 Claims, 7 Drawing Sheets

CENTRIFUGAL PARTICLE SEPARATION AND DETECTION DEVICE

BACKGROUND OF THE INVENTION

1. Field of the Invention

The present invention relates to a centrifugal particle separation and detection device, and more particularly to a centrifugal particle separation and detection device for separating particles according to the particle size.

2. The Prior Arts

Micro-electro-mechanical systems (MEMS) constitute an integrated technology applicable in multiple technical areas, and are subject to research and development. MEMS involves optical, mechanical, electric, materials science, control, chemical and biomedical technologies, which can be integrated to manufacture miniaturized products with enhanced performance, quality and reliability at a reduced cost. While micro-electronic technology provides miniaturization of electronic systems, MEMS can bring significant advances in telecommunication, consumer electronic products, industrial manufacture, biomedical techniques, green industry, defense industry, agriculture production, and aerospace industry.

MEMS techniques apply semiconductor processes to produce various miniaturized elements. In particular, MEMS technique uses photolithography processes to replicate the element to form on a silicon wafer, such that multiple miniaturized elements can be manufactured once with the same accuracy.

One attractive application of MEMS technique is to manufacture biological chips. MEMS technique can fabricate the miniaturized pumps, valves, filters, mixers, tubes, sensors, reactors and other elements needed for biological analysis on a chip. The chip can perform sample mixing, transmission, separation and detection.

Currently, micro-filters are widely used in particle or cell separation. For example, in separation or purification methods, the micro-structure is used separate particles or cells of different sizes. These methods without additional marker substances for identification, are instant to apply, and easy to operate. Currently, there are four main types of particle separation techniques using micro-structures type filter: the weir-type filter, pillar-type filter, cross-flow filter, and the membrane filter.

Particle separation can have multiple applications, for example cancer cell detection, blood and lymphocyte isolation, tissue engineering application and fine chemical purification. The sub-population of specific cells in a biological sample solution, and various sizes of particles in a max of chemical materials usually need further separation or purification for analysis. The ideal system for separating microparticles/cells should be easy to operate, does not require pre-processing of the sample treatment, and can be integrated with the conventional sample analysis system (for example, PCR, FACS). The separation of particles or cells according to the particle sizes does not require specific markers. Moreover, the ability to promptly and easily separate particles or cells plays an important factor in the implementation of separation devices. However, the current separation device is easily to be clogged, which gradually reduce the filtering efficiency. Therefore, there is a need for an improved design of the particle separation device that can improve the clog problem, and is also applicable in the fields of cancer cell detection, blood lymphocyte isolation, tissue engineering and fine chemical purification.

SUMMARY OF THE INVENTION

One aspect of the present invention is to provide a centrifugal particle separation and detection device that can improve clog problem. The centrifugal particle separation and detection device is operated with a centrifuge, and comprises a base for receiving an object to be separated and detected; at least one concentric wall disposed on the base to delimit a plurality of annular channels, the concentric wall having a plurality of apertures communicating with the annular channels; an outer wall disposed on the base and surrounding the concentric wall at an outermost periphery; and a lid upwardly covering the concentric wall and the outer wall, the lid having an inlet for loading the object to be detected; wherein the apertures through the concentric wall are identical, and the apertures through the concentric wall with a smaller inner radius are larger than the apertures through the concentric wall with a greater inner radius.

In one embodiment, the concentric wall, the outer wall, and the lid are made of polydimethylsiloxane (PDMS), the outer wall has a circular shape and is concentric to the concentric wall. Moreover, the centrifuge is operable to rotate at a speed of 1000-4000 rpm, and actually the speed can be vary by different centrifuge.

In another embodiment, the centrifuge has a rotary plate that is manually touched to stop for changing the speed instantly which can generate lateral flow among the structure and the lateral flow can significantly decreasing clogging.

The centrifugal particle separation and detection device according to the present invention can improve conventional clog problem, and has multiple applications, such as separation and detection of chemical particles or biological samples including cancer cell, microorganism, polynucleotides, and protein sample, wherein the biological sample having a target substance is specifically coupled to a bead, and the bead coupled with the target substance then is loaded in to the inlet, and the bead has an antibody coated on its surface.

The present invention is further explained in the following embodiment illustration and examples. Those examples below should not, however, be considered to limit the scope of the invention, it is contemplated that modifications will readily occur to those skilled in the art, which modifications will be within the spirit of the invention and the scope of the appended claims.

DETAILED DESCRIPTION OF THE PREFERRED EMBODIMENTS

Definition

The term "target substance" as used herein means polynucleotides, proteins, cancer cells, blood lymphocytes, microorganism and fine chemical.

Figure 1:
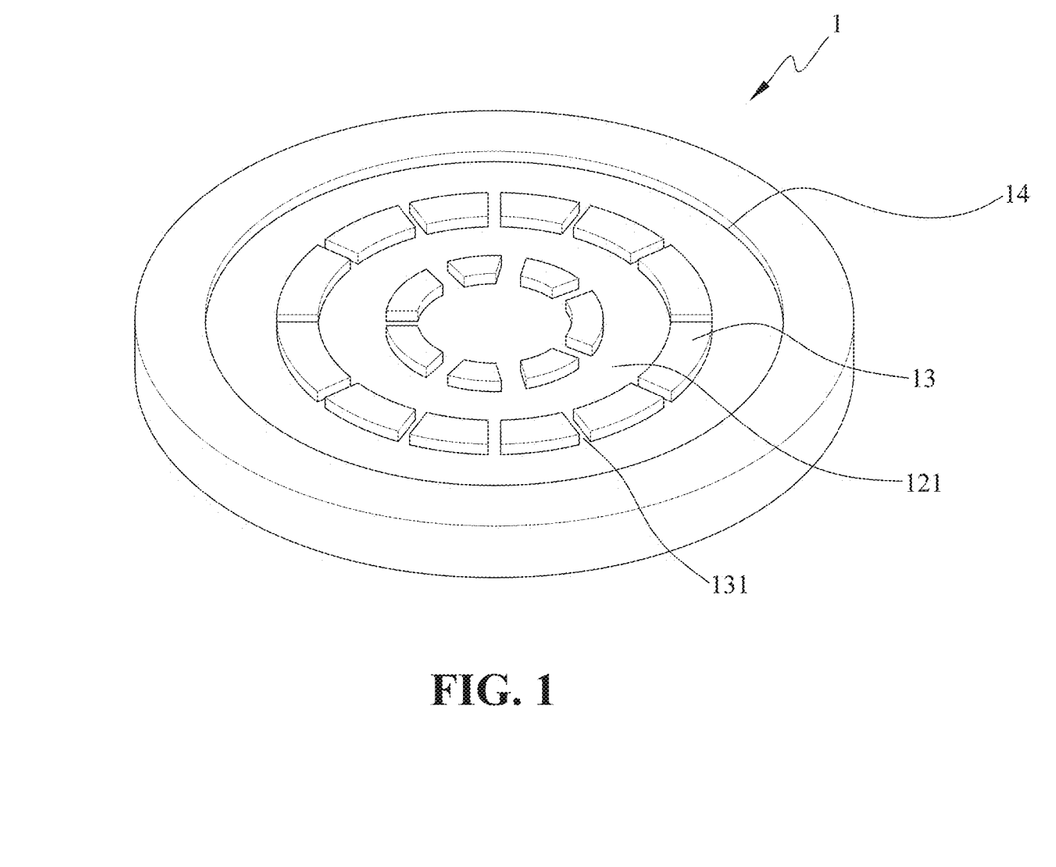
FIG. 1 is a schematic view showing a design of a centrifugal particle separation and detection device of the present invention.

FIG. 1 shows a centrifugal particle separation and detection device. The centrifugal particle separation and detection device 1 can be a concentric separation device for use with a centrifuge (not shown). An object to be detected can be coupled with particles displaced by the rotation of the centrifuge. Particles of different diameters are carried by a flow of liquid to pass through the concentric wall 13 having apertures of different sizes. Particles of a same diameter are then captured in an annular channel 121. This device can be applied for effective separation of small size and volume of particles, such as chemical particles or lymphocytes from blood samples.

Figure 2:
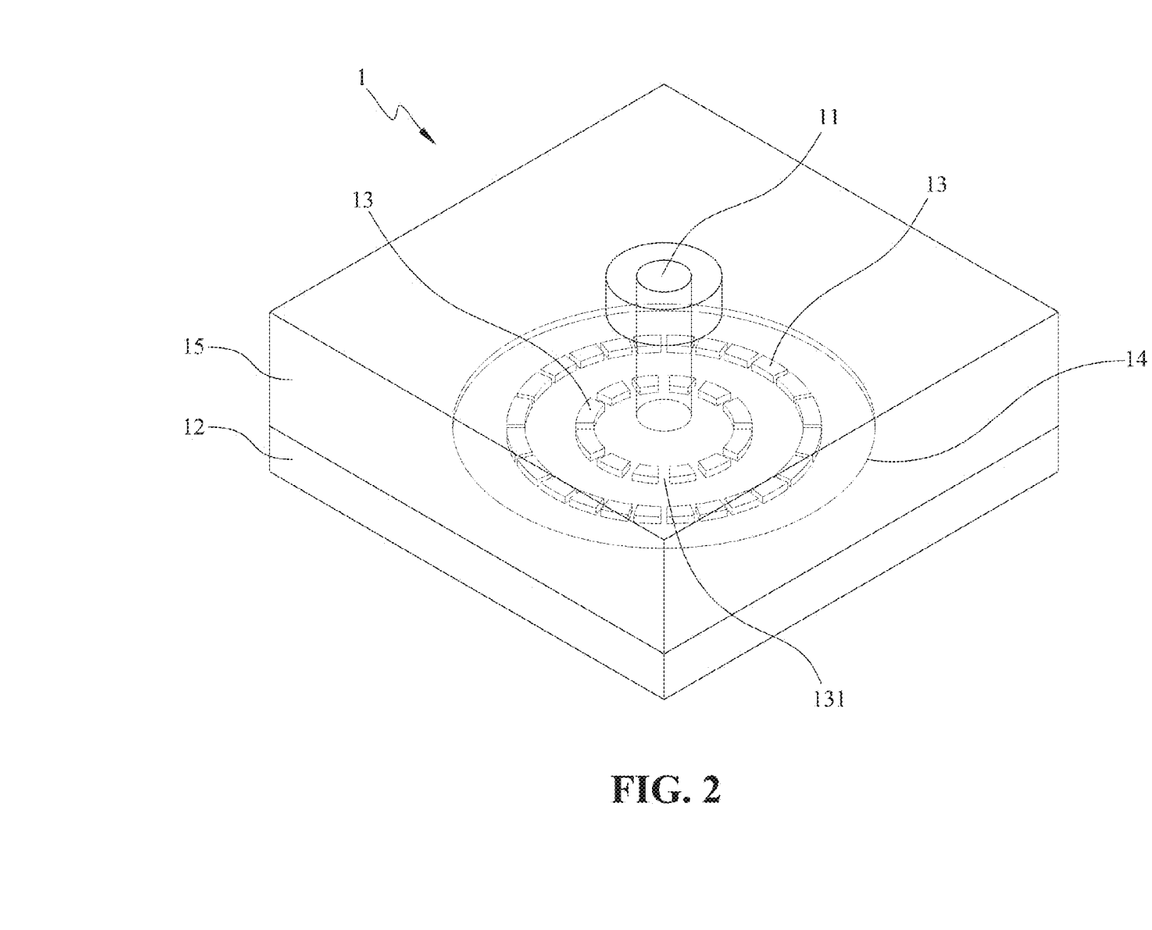
FIG. 2 is a schematic view showing a centrifugal particle separation and detection device of the present invention.

FIGS. 1 and 2 are schematic views showing the centrifugal particle separation and detection device 1. The centrifugal particle separation and detection device 1 comprises a base 12 for receiving an object to be separated and detected, at least one concentric wall 13 disposed on the base 12 to delimit a plurality of annular channels 121, the concentric wall 13 having a plurality of apertures 131 communicating with the annular channels 121; an outer wall 14 disposed on the base 12 and surrounding the concentric wall 13 at an outermost periphery; and a lid 15 upwardly covering the concentric wall 13 and the outer wall 14, the lid 15 having an inlet 11 for loading the object to be detected; wherein the apertures 131 through the same concentric wall 13 are identical, and the apertures through the concentric wall with a smaller inner radius are larger than the apertures through the concentric wall with a greater inner radius.

The concentric wall, the outer wall, and the lid of the centrifugal particle separation and detection device 1 are made of polydimethylsiloxane (PDMS). Particles are separated through the filters of different sizes (i.e. apertures) formed by the PDMS structure. The rotation speed of the centrifuge can be between 1000 and 4000 rpm or could be faster if other centrifuge is used. The higher rotation speed, the faster separation of the sample. The centrifugal particle separation and detection device 1 of the present invention can have a lowest separation speed equal to 1000 rpm. By changing the rotation speed rapidly, larger particles are washed around the annular channel by the lateral flow away from the apertures of the concentric walls, and flow along a circular path without clogging the apertures. Meanwhile, smaller particles are spin toward an outer concentric wall.

Examples of centrifugal particle separation and detection devices of the present invention are described hereafter applied for separating chemical particles and biological samples.

Example 1

Fabrication of the Centrifugal Particle Separation and Detection Device

Photolithography and soft-lithography techniques can be applied to fabricate the centrifugal particle separation and detection device 1. The concentric walls 13, outer wall 14 and lid 15 are made by replica molding of PDMS through a silicon master mold. The inlet 11 is then formed by punching and binding to the base 12. The fabrication method is described in more details hereafter.

Figure 3A:
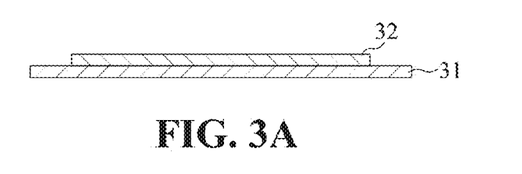
FIGS. 3A to E are cross-sectional diagrams of the manufacturing steps of the centrifugal particle separation and detection device of the present invention.

The photoresist SU-8 3050 is spin-coated on a surface of a silicon wafer 31 at a rotation speed of 3000 rpm. A transparent mask printed with a negative pattern of the device is then placed on the wafer 31, and exposed for 90 seconds to ultraviolet irradiation having a wavelength of about 334 nm. The exposed regions of the photoresist thereby become cross-linked. The uncross-linked portions of the photoresist then can be removed, so that the wafer is covered with a positive relief 32 of the photoresist as shown in FIG. 3A.

Figure 3B:
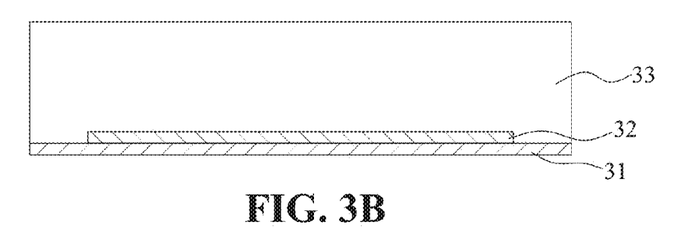

Referring to FIG. 3B, the centrifugal particle separation and detection device 1 can be made by replica molding PDMS provided by the company Dow Cornell, and curing the degassed elastomer mixture (the base to curing agent ratio is 10:1) against a silicon master at a temperature of about 80° C. degrees for about 2.5 hours. A PDMS solid piece 33 is thereby formed by polymerization, the base being made of PDMS, the curing agent being PDMS B.

Figure 3C:
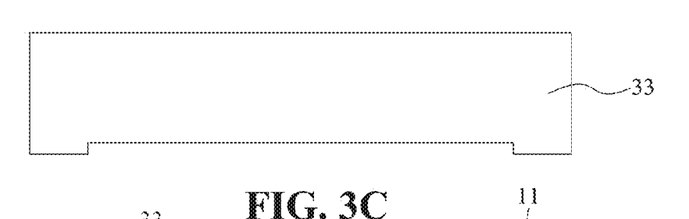
Figure 3D:
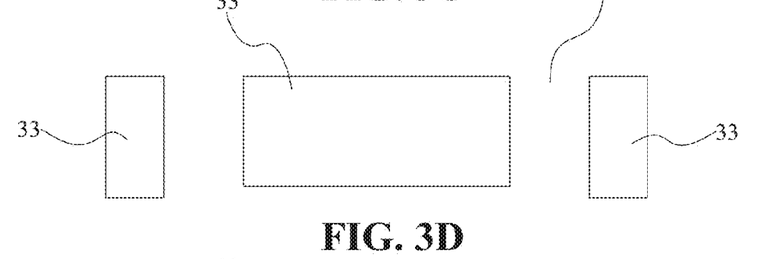
Figure 3E:
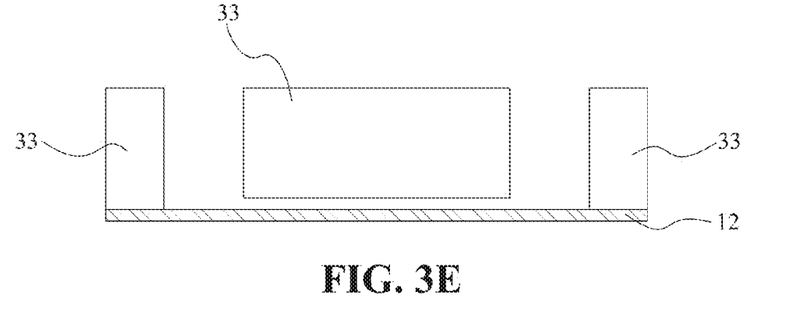

Referring to FIG. 3C, the PDMS solid piece 33 is peeled off the silicon master, and cut into individual PDMS structures. A punching tool having a diameter of about 4 mm can be used to form the inlet 11 and an outlet for exhausting the separated sample (which can be optional) as shown in FIG. 3D. The PDMS structures are air-dusted, and washed multiple times in de-ionized water and ethanol, and then dried on a hot plate. The glass base 12 is air-dusted, washed multiple times in de-ionized water and isopropanol, and then connected with an underside of the PDMS structure as shown in FIG. 3E. The surface of the PDMS structure and the glass substrate 12 are then oxidized in oxygen plasma for about 45 seconds, and then disposed on the hot plate with the pure water between PDMS and glass at about 90° C. degrees for about 30 minutes.

When the centrifugal particle separation and detection device 1 is actuated in a centrifuge, the centrifugal force will drive smaller particles through the apertures of the concentric walls, whereas larger particles are trapped in the inner area. By rapidly changing the rotation speed of the centrifuge, a lateral flow can be generated along each concentric wall. As a result, the particles can be washed around the concentric wall by the lateral flow in each channel away from the apertures of the concentric walls. The clog problem can be thereby improved. Meanwhile, the centrifugal force can drive smaller particles to flow outward through the apertures and channels, and prevent them from returning toward inner channels.

Example 2

Separation of Chemical Particles

In the present invention, the concentric walls with different aperture width. The centrifugal particle separation and detection device 1 fabricated according to Example 1 has two concentric walls 13. Each of the apertures through the inner concentric wall 13 has a width of about 40 µm, and each of the apertures through the outer concentric wall 13 has a width of about 20 µm.

Figure 4:
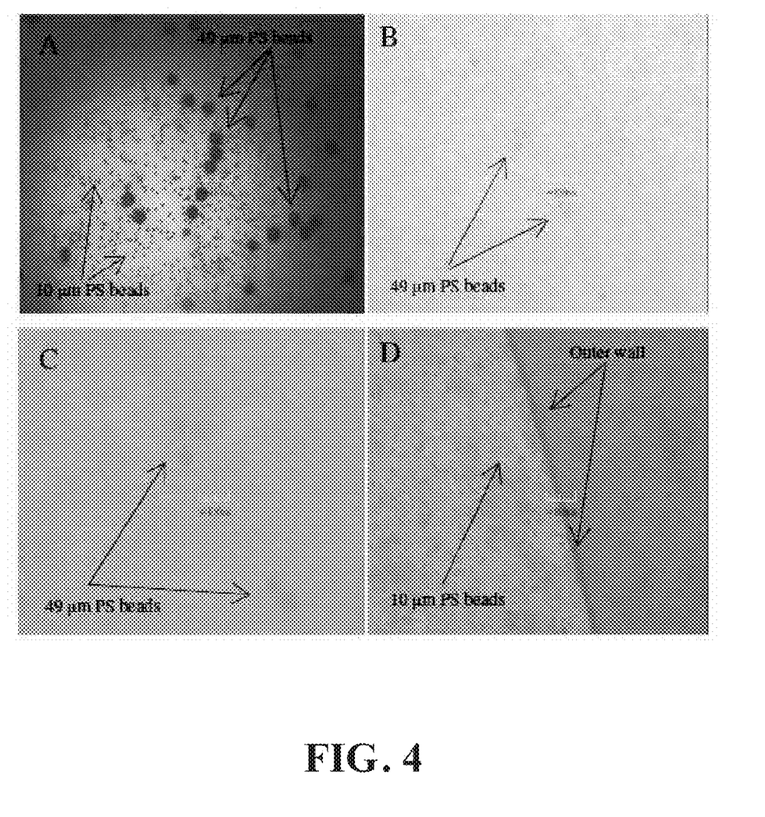
FIGS. 4A to D show the results of PS (polystyrene) beads separation performed with the centrifugal particle separation and detection device of the present invention, wherein (A) a mixture of PS beads respectively having diameters of 49 μm and 10 μm, (B) and (C) after applying centrifugation force, the 49 μm PS beads are separated by the apertures through the concentric wall with a smaller inner radius; (D) the 10 μm PS were spin outer to the outer annular channel.

A mixture of 49 µm and 10 µm polystyrene (PS) beads is used as the object to be tested. The mixture of polystyrene beads (as shown in FIG. 4A) is mixed with pure water, and then is injected into the centrifugal particle separation and detection device 1 through the inlet 11. The centrifugal particle separation and detection device 1 then is disposed in a centrifuge (for example, purchased from the company E-Centrifuge Wealtec Corp.). The centrifuge can be operated at a rotation speed of 4000 rpm for 20 seconds, after which it can be observed that beads of different sizes are separated through the apertures under the centrifugal force. The large 49 μm polystyrene beads remain in the central area of the device (as shown at B and C of FIG. 4), whereas smaller 10 μm polystyrene beads are spin out to the outer wall area (as shown at D of FIG. 4).

During the experiment, no clogging is observed, and particles can be carried by the lateral flow away from the apertures to prevent the polystyrene beads from jamming the apertures of the device. Once the separation is completed, the separated sample is exhausted from the outlet or extracted by a syringe is inserted into the different annular channel 121.

Example 3

Separation and Detection of the Biological Sample

Figure 5:
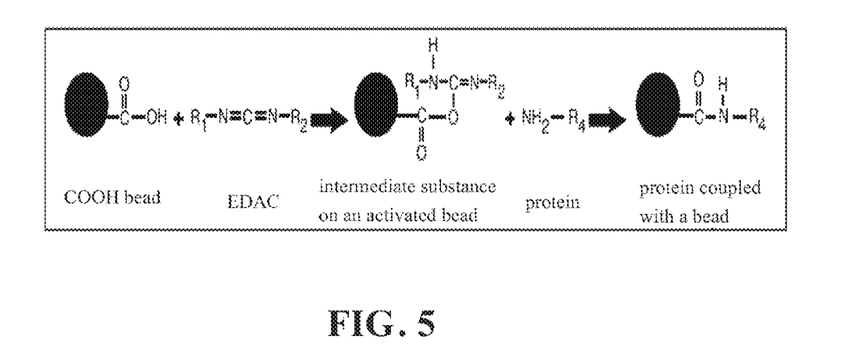
FIG. 5 shows an anti-human CD3 antibody covalently bonding with a PS bead.

The device can be used to detect biomedical particles. This Example uses PS beads sold by Polysciences Inc. under the product designation Polybead® Carboxylate Microspheres having a diameter of about 20.00 μm. Each of the PS beads has a COOH functional group which can covalently bond with an amino group of a protein. The Polylink Protein Coupling Kit sold by Polysciences Inc. is used to covalently bond an anti-human CD3 antibody with the PS bead. The bonding method is described hereafter with reference to FIG. 5.

The beads, the polylink coupling buffer and the polylink wash/storage buffer agent are warmed to room temperature. About 12.5 mg of beads is extracted via a pipet into 1.5-2 ml polypropylene centrifuge tube. The centrifuge tube then is rotated to generate a centrifugal force of about 500-1000×G for about 5-10 minutes. The resulting precipitate is resuspended in 0.4 ml of the polylink coupling buffer.

The suspension is spun with a centrifugal force of about 500-1000×G for 5-10 minutes. The precipitate is resuspended in 0.17 ml of the polylink coupling buffer.

Before the above particle suspension is used, a 200 mg/ml of EDAC solution is prepared by dissolving 10 mg of polylink EDAC in 50 μl of the polylink coupling buffer and use immediately. 20 μl of the EDAC solution is added to the particle suspension, which is then mixed gently end-over-end or briefly vortex for 15 minutes.

A protein equivalent is added to 200-500 μg. This may be prepared as 1-5 mg/ml of proteins (LEAF™ purified anti-human CD3 antibodies purchased from Biolegend, Inc.) in the coupling buffer and mixed gently end-over-end or briefly vortex. The amount of proteins bond to the beads is determined by the concentration of the proteins in the solution and the size of the beads.

The mixture is gently agitated for 30-60 minutes at room temperature. The preferred agitation is end-over-end agitation. The coupling of the proteins may be enhanced by prolonging the time of agitating the mixture.

Next the mixture is subject to a centrifuge of about 500-1000×G for 10 minutes. The supernatant liquid then is extracted to evaluate the amount of coupled proteins. The precipitate (i.e. pellet) is then resuspended in 0.4 ml of the polylink wash/storage buffer. The centrifuge and suspension steps are repeated again, after which the supernatant is extracted to evaluate the amount of coupled proteins. The beads then are stored in the polylink wash/storage buffer at 4° C.

The Jurkat human T-leukemic cell line (ATCC number TIB-152) is grown in a RPMI 1640 medium (Gibco/Invitrogen) supplemented with 10% fetal bovine serum (FBS) in a 37° C., 5% $CO_2$ incubator.

The 20 μm PS beads having surfaces coated with anti-human CD3 antibodies are added into the Jurkat cell culture, such that the PS beads are coupled with the cells. After 24 hours, the cells coupled with the PS beads are observed.

Figure 6A:
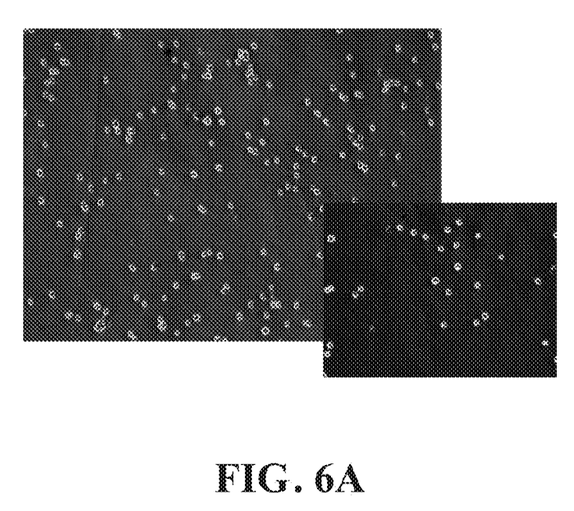
FIG. 6A shows the Jurkat human T-leukemic cell line.
Figure 6B:
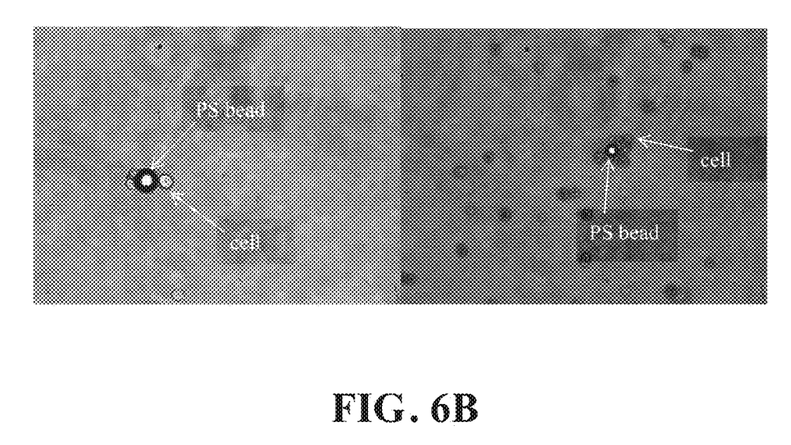
FIG. 6B shows a PS bead coupled with the Jurkat human T-leukemic cell line.

FIG. 6A shows the Jurkat human T-leukemic cell line. The above anti-human CD3 antibodies coated PS beads are coupled with the Jurkat cells having human CD3 acceptors (as shown in FIG. 6B). Then the mixture is placed in the centrifugal particle separation and detection device 1. The device 1 is rotated in a centrifuge at a speed of 4000 rpm, and after 5 seconds the user can manually touch the rotary plate of the centrifuge to immediately stop it. The same steps are repeated 5 times or more. The mixture including the PS beads having the anti-human CD3 antibodies and the Jurkat cell culture is loaded into the inlet such as a liquid slot of the device 1, which is spun in a small centrifuge, such as the one sold by E-CentrifugeWealtect Corp. The rotation speed of the centrifuge at rated is about 4000 rpm and the relative centrifuge force is about 2000 g.

In one example, the centrifugal particle separation and detection device 1 used to separate the cells has two concentric walls 13. The apertures 131 in the inner concentric wall 13 have a size of 25 μm, and the apertures 131 in the outer concentric wall 13 have a size of 15 μm. The size of the apertures 131 can be determined according to the size of the particles to separate from the sample. The width of the annular channel 121 can be determined according to the amount of the particles in the sample.

Figure 7A:
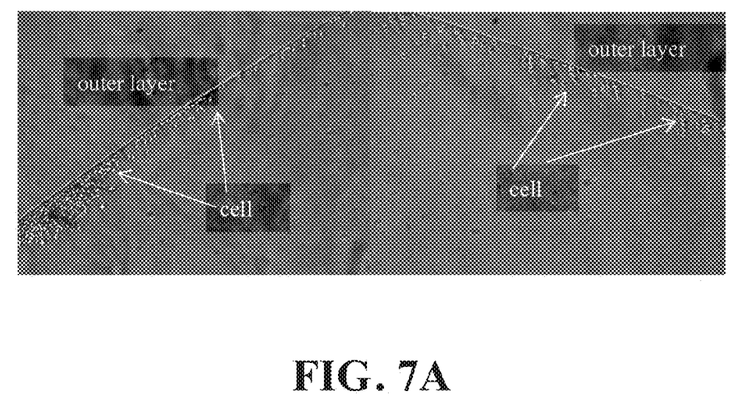
FIGS. 7A to B show the results of cell separation experiments.
Figure 7B:
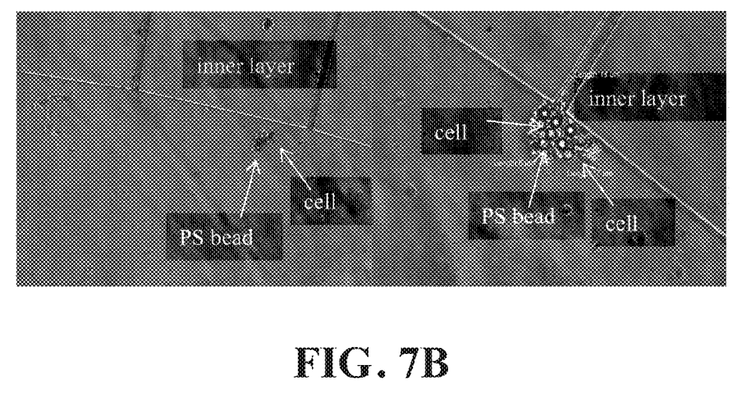

The result shows that the cells not coupled with the PS beads are spun out to the outer wall area of the device (as shown in FIG. 7A), and the Jurkat human T-leukemic cell line that are coupled with the PS beads are retained in the inner area of the device and can be easily observed since the inner area is small (as shown in FIG. 7B). The experiment shows that the device 1 used in combination with functional particles can effectively separate cancer cells or other desirable types of cells and also be applied to separate polynucleotides, proteins, and microorganism.

The centrifugal particle separation and detection device can be manufactured by using a standard PDMS modular process. Therefore, the manufacture cost is low, and convenient to achieve. Moreover, various sizes of particles can be effectively separated without clog problem.

The centrifugal particle separation and detection device can also be designed with various sizes of annular channels and apertures to separate different sizes of particles. The number of concentric walls 13 can also be increased to reduce the size difference for particles separated in a same region. The device can be used in testing of blood samples, separation of blood cells, detection of cancer cells, polynucleotide hybridization, tissue engineering, microorganism and purification of fine chemical and biological diagnosis.

What is claimed is:

1. A method of particle separation using a centrifuge and a centrifugal and detection device disposed thereon, comprising:

putting an object to be separated and detected into a base of the centrifugal and detection device, wherein the centrifugal and detection device comprises at least two concentric walls disposed on the base to delimit a plurality of annular channels, an outer wall disposed on the base and surrounding the concentric walls at an outermost periphery, and a lid upwardly covering the concentric walls and the outer wall, the lid having an inlet for loading the object to be detected, wherein the concentric walls comprises a plurality of apertures communicating with the annular channels:

rotating the centrifuge to allow the object to move through the annular channels and the apertures according to its size;

intermittently manually touching a rotary plate of the centrifuge to instantly stop the centrifuge, thereby generating a lateral flow for decreasing clogging during the rotating step; and resulting in a target substance of the object being retained in an inner annular channel after centrifugation, wherein the object is directly loaded to a central annular channel through the inlet;

wherein the at least two concentric walls comprises a first concentric wall and a second concentric wall, wherein an inner radius of the second concentric wall is greater than an inner radius of the first concentric wall, wherein all of the apertures through the first concentric wall are identical in size and all of the apertures through the second concentric wall are identical in size, and the apertures through the first concentric wall are larger than the apertures through the second concentric wall.

2. The method of claim 1, wherein the centrifuge is operable to rotate at a speed of 1000-4000 rpm.

3. The method of claim 1, wherein the object to be detected is a chemical particle.

4. The method of claim 1, wherein the object to be detected is a biological sample.

5. The method of claim 4, wherein the biological sample is a cancer cell sample, a polynucleotide sample, a protein sample and a microorganism sample.

6. The method of claim 4, wherein the biological sample having a target substance is specifically coupled to a bead and then the bead coupled with the target substance is loaded in to the inlet.

7. The method of claim 6, wherein the bead has an antibody coated on its surface.

8. The method of claim 1, wherein the outer wall has a circular shape and is concentric to the concentric wall.

9. The method of claim 1, wherein the concentric wall, the outer wall, and the lid are made of polydimethylsiloxane (PDMS).

* * * * *